United States Patent [19]

Summers et al.

[11] Patent Number: 5,120,751
[45] Date of Patent: Jun. 9, 1992

[54] BENZOYLPHENYL PYRIDINYLTHIAZOLIDINE COMPOUNDS AS PLATELET ACTIVATING ANTAGONISTS

[75] Inventors: James B. Summers, Libertyville; Douglas H. Steinman, Morton Grove; Denise E. Guinn, Grayslake; Steven K. Davidsen, Mundelein, all of Ill.; Paul D. May, Bristol, Wis.

[73] Assignee: Abbott Laboratories, Abbott Park, Ill.

[21] Appl. No.: 677,687

[22] Filed: Mar. 29, 1991

[51] Int. Cl.$^5$ .................. C07D 417/04; A61K 31/44
[52] U.S. Cl. ............................... 514/342; 514/343; 514/336; 546/280; 546/281; 546/284
[58] Field of Search .................. 546/280; 514/342

[56] References Cited

U.S. PATENT DOCUMENTS

| | | | |
|---|---|---|---|
| 4,786,645 | 11/1988 | Fabre et al. | 514/333 |
| 4,940,709 | 7/1990 | Shimazaki et al. | 514/253 |
| 4,948,795 | 8/1990 | Toshiyasu Mase et al. | 514/252 |

FOREIGN PATENT DOCUMENTS

| | | |
|---|---|---|
| 0279681 | 8/1988 | European Pat. Off. . |
| 0350145 | 1/1990 | European Pat. Off. . |

*Primary Examiner*—Jane T. Fan
*Attorney, Agent, or Firm*—Jerry F. Janssen

[57] ABSTRACT

Benzoylphenyl derivatives of 2-(3-pyridinyl)-3-alkyl-4-thiazolidinecarboxamide, 2-(3-pyridinyl)-thiazolid-4-ylacetamide, 2-(3-pyridinyl)-4-dithiolanecarboxamide or 2-(3-pyridinyl)dithiolan-4-yl] urea are potent inhibitors of PAF and are useful in the treatment of PAF-related disorders including anaphylactic shock, respiratory distress syndrome, acute inflammation, delayed cellular immunity, parturtition, fetal lung maturation, and cellular differentiation.

6 Claims, No Drawings

BENZOYLPHENYL PYRIDINYLTHIAZOLIDINE COMPOUNDS AS PLATELET ACTIVATING ANTAGONISTS

TECHNICAL FIELD

This invention relates to compounds having pharmacological activity, to compositions containing these compounds, and to a medical method of treatment employing the compounds and compositions. More particularly, this invention concerns certain benzoylphenyl pyridylthiazolidine compounds and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

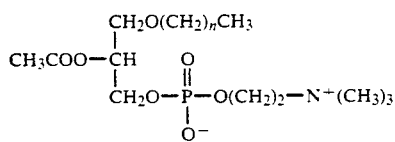

where n is the integer 15 or 17.

PAF is physiologically active and causes contraction of the airway smooth muscle, increased vascular permeability, platelet aggregation and hypotension and the like. It is now recognized as a powerful mediator of inflammation and may play a physiological or pathobiologic role in a variety of clinical conditions, such as asthma and pulmonary dysfunction, acute inflammation, transplanted organ rejection, endotoxin and IgG-induced shock, thrombosis, cardiac anaphylaxis, gastrointestinal ulceration, allergic skin diseases, retinal and corneal diseases, chemically induced liver cirrhosis, and ovimplantation in pregnancy.

Several anti-PAF agonists have been reported (e.g., U.S. Pat. No. 4,948,795, European Patent Application EP 279681, and U.S. Pat. No. 4,786,645) but none have received wide acceptance. Therefore, there is a continuing need for the development of potent, orally active antagonists of PAF which have low toxicity.

SUMMARY OF THE INVENTION

The present invention provides, in its principal aspect, compounds having PAF antagonist activity and possessing the structural formula:

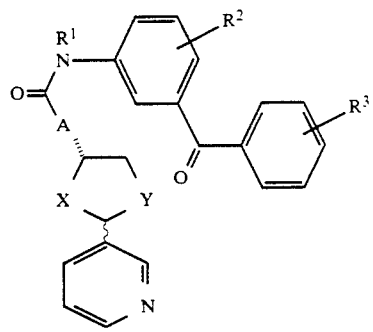

in which $R^1$ is hydrogen or alkyl of from one to six carbon atoms.

$R^2$ is one, two, or three substituents selected from hydrogen, halogen, or alkyl of from one to six carbon atoms.

$R^3$ is one, two, or three substituents selected from hydrogen, halogen, or alkoxy of from one to six carbon atoms.

A is a valence bond, or is selected from the group consisting of methylene and $>NR^4$ where $R^4$ is hydrogen or alkyl of from one to six carbon atoms with the provision that when X is $>NH$ or nitrogen substituted with alkyl of from one to six carbon atoms, A cannot be $>NR_4$.

X is sulfur or $>NR^5$ where $R^5$ is hydrogen, alkyl of from one to six carbon atoms, alkoyl of from one to six carbon atoms, $-C(O)NR^6R^7$ where $R^6$ and $R^7$ are independently selected from hydrogen and alkyl of from one to six carbon atoms, or $-C(O)OR^8$ where $R^8$ is alkyl of from one to six carbon atoms.

Y is sulfur or methylene.

The compounds of the present invention contain one or more asymmetric carbon centers, particularly at the site of attachment of the group Y to the five-membered ring containing X and Y, and are thus capable of existence in stereoisomeric forms. The pharmaceutically acceptable salts, and individual stereoisomers of compounds of structural formula I above, as well as mixtures thereof, are also contemplated as falling within the scope of the present invention.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment a PAF-inhibiting effective amount of a compound of structure I above.

In yet another aspect of the present invention, there is provided a method of treating PAF-mediated disorders including asthma, shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION AND PREFERRED EMBODIMENTS

In one embodiment of the present invention, represented by Formula II, A is a valence bond, X is NH, Y is sulfur, and $R^1$, $R^2$ and $R^3$ are defined as above.

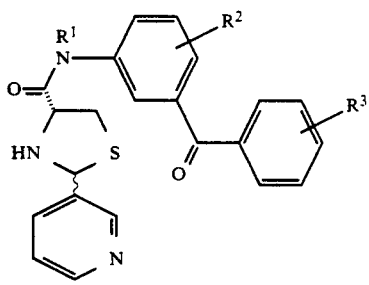

Preferred compounds of Formula II are those in which $R^1$ and $R^2$ are hydrogen or lower alkyl and $R^3$ is hydrogen or lower alkoxy. Particularly preferred compounds of Formula II are those in which $R^1$ are hydrogen or methyl, $R^2$ is hydrogen, and $R^3$ is hydrogen, 3,4-dimethoxy, 3,5-dimethoxy, or 3,4,5-trimethoxy.

In another embodiment, compounds of the present invention are represented by Formula III in which A is a valence bond, both X and Y are sulfur, and $R^1$, $R^2$ and $R^3$ are defined as above.

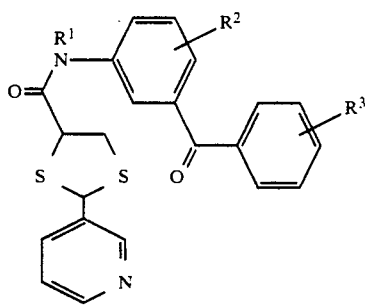

Preferred compounds of Formula III are those in which $R^1$ and $R^2$ are hydrogen and $R^3$ is hydrogen or lower alkoxy. Particularly preferred compounds of Formula III are those in which $R^1$ and $R^2$ are hydrogen, and $R^3$ is 3,4,5-trimethoxy.

In yet another embodiment, compounds of the present invention are represented by Formula IV in which A is >NH, both X and Y are sulfur, and $R^1$, $R^2$ and $R^3$ are defined as above.

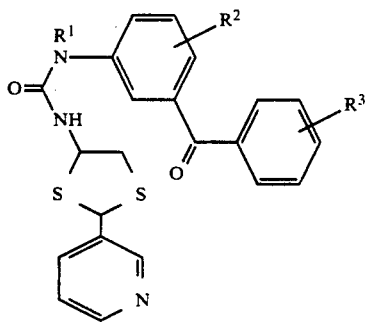

The preferred compounds of Formula IV are those in which $R^1$ and $R^2$ are hydrogen and $R^3$ is hydrogen or lower alkoxy. Particularly preferred compounds of Formula IV are those in which $R^1$ and $R^2$ are hydrogen, and $R^3$ is 3,4,5-trimethoxy.

Examples of compounds contemplated as falling within the scope of the present invention include, but are not necessarily limited to:

N-(3-benzoylphenyl) 2-(3-pyridinyl)-4-thiazolidine carboxamide;

N-(3-benzoylphenyl) 2-(3-pyridinyl)-3-tert-butoxycarbonyl-4-thiazolidinecarboxamide;

N-[3-(4-methoxybenzoyl)phenyl] 2-(3-pyridinyl)-4-thiazolidinecarboxamide;

N-[3-(3,4-dimethoxybenzoyl)phenyl] 2-(3-pyridinyl)-4-thiazolidinecarboxamide;

N-[3-(3,5-dimethoxybenzoyl)phenyl] 2-(3-pyridinyl)-4-thiazolidinecarboxamide;

N-[3-(3,4,5-trimethoxybenzoyl)phenyl] 2-(3-pyridinyl)-4-thiazolidincarboxamide;

N-(3-benzoylphenyl) N-methyl 2-(3-pyridinyl)-4-thiazolidinecarboxamide;

N-(3-benzoylphenyl) 2-(3-pyridinyl)-3-formyl-4-thiazolidinecarboxamide;

N-(3-benzoylphenyl) 2-(3-pyridinyl)-3-(N-methylcarbamoyl)-4-thiazolidinecarboxamide;

N-(3-benzoylphenyl) 2-(3-pyridinyl)-thiazolid-4-ylacetamide;

N-(3-benzoylphenyl) 2-(3-pyridinyl)-3-carbamoyl-thiazolid-4-ylacetamide;

N-(3-benzoylphenyl) 2-(3-pyridinyl)-3-tert-butoxycarbonyl-lthiazolid-4-ylacetamide;

N-(3-benzoylphenyl]) 2-(3-pyridinyl)-4-dithiolanecarboxamide;

N-[3-(3,4,5-trimethoxybenzoyl)phenyl] 2-(3-pyridinyl)-4-dithiolanecarboxamide;

N-(3-benzoylphenyl) N'-[2-(3-pyridinyl)dithiolan-4-yl] urea;

N-[3-(3,4,5-trimethoxybenzoyl)phenyl] N'-8 2-(3-pyridinyl)dithiolan-4-yl] urea;

N-methyl-N-(3-benzoylphenyl) N'-[2-(3-pyridinyl)dithiolan-4-yl] urea;

N-methyl-N-[3-(3,4,5-trimethoxybenzoyl)phenyl] N'-[2-(3-pyridinyl)dithiolan-4-yl] urea;

and their pharmaceutically acceptable salts.

As used throughout this specification and the appended claims, the following terms have the meanings ascribed to them:

The term "alkoxy" as used herein refers to a lower alkyl group, as defined herein, which is bonded to the parent molecular moiety through an oxygen atom Representative examples of alkoxy groups include methoxy, ethoxy, t-butoxy, and the like.

The term "alkoyl" as used herein refers to formyl and radicals of the structure —C(O)-alkyl in which the alkyl portion is a straight or branched alkyl group of from one to six carbon atoms. Representative examples of alkoyl groups include formyl, acetyl, propionyl, butyryl, isobutyryl, pivaloyl, and the like.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "carbamoyl" is used herein to mean —$CONR^6R^7$ werein $R^6$ and $R^7$ are independently, hydrogen or a lower alkyl radical. Representative examples of carbamoyl groups, include carbamoyl, dimethyl-carbamoyl, tert-butylcarbamoyl, methyl ethylcarbamoyl and the like.

The term "carboalkoxy" is used herein to mean —C(O)OR$^8$ wherein R$^8$ is an alkyl radical. Representative examples of carboalkoxy groups include carbomethoxy, carboethoxy, carboisopropoxy, carbobutoxy, carbosecbutoxy, carboiso-butoxy, carbotertbutoxy, and the like.

The term "halogen" refers to fluorine, chlorine or bromine.

The terms "PAF-related disorders" and "PAF-mediated disorders" are used herein to mean disorders related to PAF or mediated by PAF, including asthma, shock, respiratory distress syndromes, acute inflammation delayed cellular immunity, parturition, fetal lung maturation, and cellular differentiation.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66: 1-19 (1977) which is incorporated herein by reference.)

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstition into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally, dosage levels of about 0.001 to about 100, more preferably of about 0.01 to about 20, and most preferably about 0.1 to about 10 mg of active compound per kilogram of body weight per day are administered orally to a mammalian patient. If desired, the effective dosage may be divided into multiple doses for purposes of administration, e.g. two to four separate doses per day.

In general, the compounds of this invention are synthesized by reaction schemes I through XII as illustrated below. It should be understood that X, Y, A, $R_1$, and $R_2$ as used herein correspond to the groups identified by Formula I.

The compounds of Formula (I–IV) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgement as to the order of synthetic steps, protecting groups required and deprotection conditions.

Individual stereoisomers of compounds of the present invention are prepared, in appropriate cases by using stereospecific reaction sequences employing resolved starting materials or are prepared by reactions which produce mixtures of the enantiomers followed by separation of the desired stereoisomers by methods well known in the art. Mixtures of diastereomers are separated, for example by fractional recrystallization or by chromatographic separation. Alternatively, a mixture of enantiomers can be converted to a mixture of diastereomeric salts by reaction of a basic center in the molecule with a resolved acid. The mixture of diastereomers is then separated by recrystallization or chromatography followed by treatment of each of the separated disatereomers with base to recover the parent compound in optically resolved state. In another alternative method, mixtures of enantiomers can be separated by chromatographic means on a chiral absorption medium using techniques known in the art.

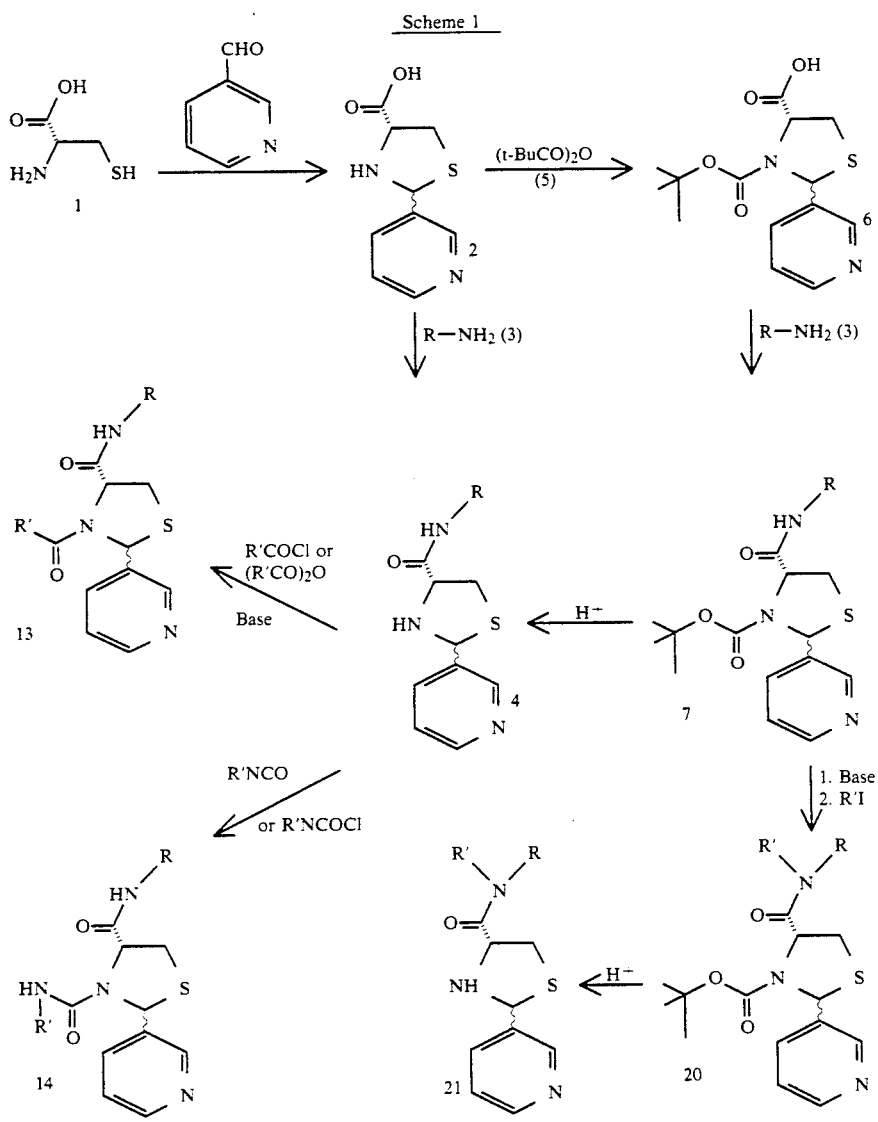

Scheme 1

SCHEME I

According to the foregoing reaction Scheme I, L-cysteine (1) is condensed with 3-pyridine aldehyde to produce 2-(3-pyridinyl)-4-thiazolidinecarboxylic acid (2). The thiazolidine nitrogen may be protected with an appropriate group, preferably carbo-tert-butoxy (BOC) with di-tert-butyl dicarbonate (5), to afford 6. The protected acid is coupled to an amine (3) using a coupling agent such as dicyclohexylcarbodiimide or BOPCl (bis(2-oxo-3-oxazolidinyl)phosphinic chloride) to yield the amide 7. The protecting group is removed under the appropriate conditions, as in the use of HCl to remove the BOC, and the amide 4 is obtained. Alternatively 2 may be coupled with 3 in the manner described above to afford 4 without protecting the thiazolidine nitrogen.

Amide 7 can further be treated with a strong base such as lithium hexamethyldisilazide followed by an alkyl halide to afford alkylated amide 20. The BOC protecting group is removed with acid to produce 21.

2-(3-pyridinyl)-4-thiazolidinecarboxamide (4) can further be treated with an acid chloride, acid anhydride or other activated acid derivative in the presence of a base such as triethylamine to afford 13. In a similar manner 4 may be treated with an isocyanate or carbamoyl chloride to afford a urea 14.

Scheme 2

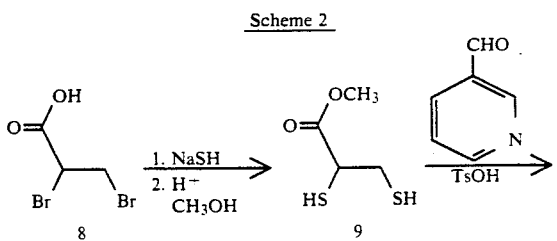

-continued
Scheme 2

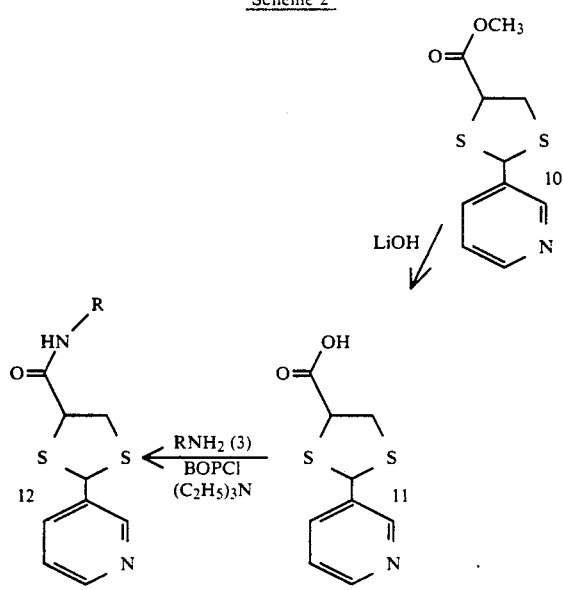

SCHEME 2

According to the foregoing reaction Scheme 2, 2,3-dibromopropionic acid (8) is treated with sodium bisulfide (NaSH) followed by esterification with HCl in methanol to give methyl 2,3-dimercaptopropenoate (9). This dithiol (9) is condensed with 3-pyridine carboxaldehyde in the presence of an acid catalyst, preferably p-toluenesulfonic acid, to afford methyl 2-(3-pyridinyl)-4-dithiolanecarboxylate (10). The dithiolane ester is hydrolyzed to the corresponding acid (11) by treatment with aqueous base, preferably lithium hydroxide. This acid is coupled to an amine (3) using a coupling agent such as dicyclohexylcarbodiimide or BOPCl (bis(2-oxo-3-oxazolidinyl)phosphinic chloride) to yield the amide 12.

SCHEME 3

According to the foregoing reaction Scheme 3, a protected 2-(3-pyridinyl)-4-thiazolidinecarboxylic acid, such as the BOC protected 6 (prepared as described in Scheme 1) is activated (for example as a mixed anhydride with iso-butyl chloroformate) and then treated with diazomethane to afford the diazoketone 15. Reaction with silver benzoate in methanol, results in rearrangement to produce the ester 16 which is hydrolyzed with base, preferably lithium hydroxide, to afford the acid 17. This acid is coupled to the amine (3) using a coupling agent such as dicyclohexylcarbodiimide or BOPCl (bis(2-oxo-3-oxazolidinyl)phosphinic chloride) to yield the amide 18. Finally the protecting group is removed under the appropriate conditions, as in the use of HCl to remove the BOC group and yield 19.

Scheme 4

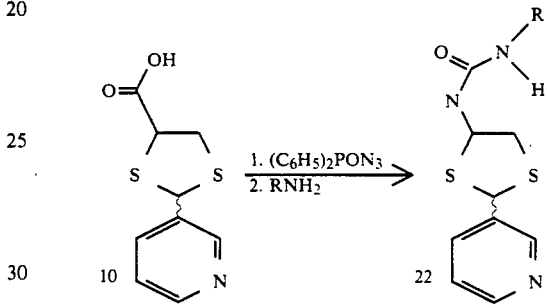

SCHEME 4

According to the foregoing reaction scheme 4, dithiolane acid 10 is heated with diphenylphosphorylazide followed by reaction with an amine (3) to produce 22.

Scheme 3

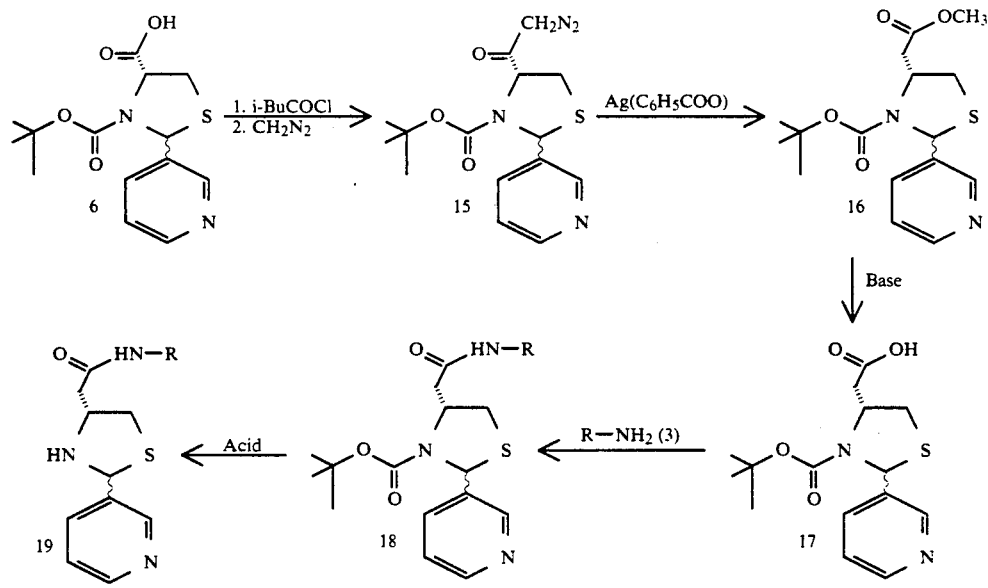

Scheme 5

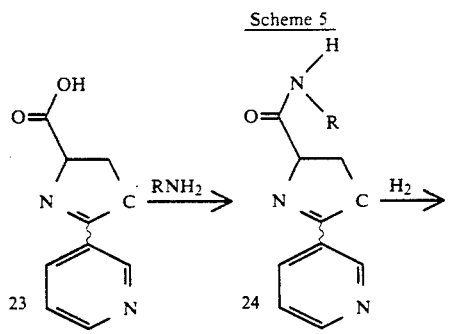

SCHEME 5

According to the foregoing reaction scheme 5, dehydro-2-(3-pyridyl)-5-pyrrolidinecarboxylic acid, 23, is coupled with an amine 3 using a coupling agent such as dicyclohexylcarbodiimide or BOPCl to yield 24. This is reduced with hydrogen in the presence of a palladium or platinum catalyst to afford the pyrrolidine.

PAF INHIBITORY ACTIVITY OF THE COMPOUNDS OF THE PRESENT INVENTION

The ability of representative compounds of the present invention to inhibit PAF activity was determined in an in vitro test using the following method.

Citrated whole rabbit blood was obtained from Pel-Freez (Rogers, AR). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM MgCl$_2$/2 mM EDTA (TME buffer, pH 7.0) with 0.25M sucrose added for membrane stabilization.

The standard PAF receptor binding assay contained 10 μg platelet membrane protein, 0.6 nM [$^3$H]C$_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Millititre-GV ™ (Millipore Corp.) filtration plates; incubation time was for 60 minutes at room temperature (22°–23° C.). "Specific binding" was operationally defined as the arithmetic difference between "total binding" of 0.6 nM [$^3$H]C$_{18}$-PAF (in the absence of added PAF) and "nonspecific binding" (in the presence of 1 μM PAF). After the prescribed incubation, platelet membranes were filtered under vacuum, and washed with 1 millilitre of "binding buffer". The filters were dried and removed. The bound radioactivity was quantitated with a Berthold TLC-Linear Analyzer model LB2842.

Dose-response curves of inhibition of specific [$^3$H]C$_{18}$-PAF binding by test compounds were conducted in triplicate, with at least four doses covering the active range. Experiments were repeated at least once. IC$_{50}$ values (concentration producing 50% inhibition) were determined by point-to-point evaluation. K$_i$ values of inhibitory binding constants were calculated according to the method of Cheng and Prusoff[Biochem. Pharmacol. 22(1973) 3099–3108] whereby $$K_i = \frac{IC_{50}}{1 + ([[^3H]PAF]/K_d[^3H]PAF)}$$
$$= \frac{IC_{50}}{1 + (0.6 \text{ nM}/0.6 \text{ nM})}$$
$$= \frac{IC_{50}}{2}$$

The values of K$_i$ for representative compounds of the present invention appear in Table 1.

TABLE 1

| PAF Receptor Binding Activity | | | | | |
|---|---|---|---|---|---|
| Example | K$_i$ (nM) | Example | K$_i$ (nM) | Example | K$_i$ (nM) |
| 1 | 5 | 8 | 6 | 15 | 620 |
| 2 | 100.000 | 9 | 23 | 16 | 2,600 |
| 3 | 5 | 10 | 570 | 17a | 1,300 |
|  |  |  |  | 17b | 260 |
| 4 | 1 | 11 | 500 | 18a | 650 |
|  |  |  |  | 18b | 35 |
| 5 | 34 | 12 | 700 | 19a | 2,900 |
|  |  |  |  | 19b | 7,000 |
| 6 | 33 | 13 | 5,800 | 20a | 260 |
|  |  |  |  | 20b | 2,200 |
| 7 | 2 | 14 | 150 | 21 | 780 |

The foregoing may be better understood from the following examples, which are presented for the purpose of illustration and not intended to limit the scope of the inventive as it is defined by the appended claims.

EXAMPLE 1

Preparation of N-(3-benzoylphenyl) 2-(3-pyridinyl)-4-thiazolidine carboxamide

Step 1. 2-(3-pyridinyl)-4-thiazolidinecarboxylic acid

Cysteine (24.2 g, 0.2 mole) and 3-pyridine carboxaldehyde (21.4 g, 0.2 mmole) were suspended in 60% aqueous ethanol (400 mL) and the mixture was heated at 100° C. for 5 hours. The reaction mixture was then cooled and most of the solvent was removed in vacuo. The resulting slurry was washed with ethanol and filtered. This material was dried overnight in vacuo at 50° C. to afford the thiazolidine acid (34 g, 81%).

Step 2. N-(3-benzoylphenyl) 2-(3-pyridinyl)-4-thiazolidine carboxamide

Dicyclohexyl carbodiimide (DCC, 3.4 g, 16.7 mmole) was added to a solution of the thiazolidine acid prepared as described above in step 1 (2.3 g, 11 mmole), 3-aminobenzophenone (2.2 g, 11 mmole), and 1-hydroxybenzotriazole hydrate (HOBT, 1.5 g, 11 mmole) in dimethylformamide (25 mL). The reaction mixture was stirred for 20 hours at room temperature and then water (5 mL) was added to quench the excess DCC. Twenty minutes later ethylacetate was added and the mixture filtered to remove dicyclohexyl urea. The filtrate was washed with saturated sodium bicarbonate, water and saturated sodium chloride the dried over magnesium sulfate. The solvent was removed in vacuo and the residue chromatographed on 200 g silica gel eluting with 5% methanol in methylene chloride to yield the desired product (1.7 g, 40%). MS (DCI-NH₃) m/e:386 (M+1)⁺; ¹H NMR (CDCl₃) d 3.43–3.62 (c, 1.5H), 3.82 (dd, 0.5H, J=4.5, 12), 4.20–4.30 (c, 0.5H), 4.54 (m, 0.5H, J=4.0), 4.98 (d, 0.5H, J=12), 5.72 (bs, 0.5H), 7.32–7.62 (c, 7H) 7.76–8.05 (c, 6H), 8.53 (dd, 0.5H, J=2,5), 8.62 (dd, 0.5H, J=2,5), 8.80 (b s, 0.5H), 9.28 (s, 0.5H).

EXAMPLE 2

Preparation of N-(3-benzoylphenyl) 2-(3-pyridinyl)-3-tert-butoxycarbonyl-4-thiazolidinecarboxamide

Step 1. 2-(3-pyridinyl)-3-tert-butoxycarbonyl-4-thiazolidinecarboxylic acid

To a slurry of 2-(3-pyridinyl)-4-thiazolidinecarboxylic acid (7.0 g; 33.3 nmol.), prepared as in Example 1, Step 1, in dioxane (40 mL) at 0° C. was added aqueous NaOH (60 mL, 1M), followed by a solution of di-tert-butyl dicarbonate (1.5 eq; 10.9 g) and dioxane (20 mL) in one portion. The resulting yellowish solution was stirred while warming to room temperature over a period of 19 hours. The resulting solution was concentrated on a rotory evaporator and then the residue was partitioned between ethyl acetate (100 mL) and water (100 mL). The aqueous phase was washed with ethyl acetate and then acidified to a pH of 4 with aqueous hydrochloric acid at 0° C. This solution was then extracted with ethyl acetate and dried over magnesium sulfate to yield 2-(3-pyridinyl)-3-tert-butoxycarbonyl-4-thiazolidinecarboxylic acid (8.27 g, 80% yield) as a white solid.

Step 2. N-(3-benzoylphenyl) 2-(3-pyridinyl)-3-tert-butoxycarbonyl-4-thiazolidinecarboxamide To a solution of 2-(3-pyridinyl)-3-tert-butoxycarbonyl-4-thiazolidinecarboxylic acid (944 mg; 1.2 eq.; 3.05 mmoL), prepared as described above, and 3-aminobenzophenone (500 mg; 2.54 mmol) in methylene chloride (0.15M) was added triethylamine (0.46 mL) at room temperature under nitrogen with stirring, followed by addition of bis(2-oxo-3-oxazolidinyl)phosphinic chloride (773 mg; 1.2 eq) and the resulting mixture was stirred at ambient temperature for 16 hours. This mixture was concentrated to an oil on a rotory evaporator which was partitioned between ethyl acetate (30 mL) and sodium bicarbonate (30 mL). The aqueous phase was extracted twice with ethyl acetate and the resulting combined organic layers were washed with brine and dried magnesium sulfate. After filtering, the solvent was removed to yield the title compound (1.43 g) as a thick orange oil. The compound was further purified by flash chromatography on silica gel to yield 1010 mg (82% yield) N-(3-benzoylphenyl) 2-(3-pyridinyl)-3-tert-butoxycarbonyl-4-thiazolidinecarboxamide as a white foam.

EXAMPLE 3

Preparation of N-(3-benzoylphenyl) 2-(3-pyridinyl)-4-thiazolidine carboxamide dihydrochloride N-(3-benzoylphenyl) 2-(3-pyridinyl)-3-tert-butoxycarbonyl-4-thiazolidinecarboxamide (1000 mg; 2.05 mmoL), prepared as described in Example 2, was mixed with a solution of hydrochloric acid in dioxane (15 mL of 4M) under nitrogen and the resulting mixture stirred at room temperature for 2 hours, followed by concentration on a rotory evaporator and partitioning the residue between ethyl acetate and saturated aqueous sodium bicarbonate. Solid sodium carbonate was added to the two phase mixture until the pH was greater than 8. The layers were separated, the aqueous phase extracted with ethyl acetate, and the resulting organic layer dried over magnesium sulfate. The mixture was then filtered and concentrated to a yellowish oil. The oil was purified by flash chromatography on silica gel to yield 732 mg (92%) of the thiazolidinecarboxamide as a white foam. The material was taken up in dioxane and stirred at room temperature with HCl in dioxane (2 mL of 4M) added dropwise. The heterogeneous reaction mixture was then stirred at room temperature for 5 minutes, concentrated in vacuo to yield N-(3-benzoylphenyl) 2-(3-pyridinyl)-4-thiazolidine carboxamide dihydrochloride as a white solid (800 mg). MS (DCI-NH₃) m/e: 386 (M+1)⁺; 1H NMR (CDCl₃) δ3.43–3.62 (c, 1.5H), 3.82 (dd, 0.5H, J=4.5,12), 4.20–4.30 (c, 0.5H), 4.54 (m, 0.5H, J=4.0), 4.98 (d, 0.5H, J=12), 5.72 (bs, 0.5H), 7.32–7.62 (c, 7H) 7.76–8.05 (c, 6H), 8.53 (dd, 0.5H, J=2, 5), 8.62 (dd, 0.5H, J=2, 5), 8.80 (b s, 0.5H), 9.28 (s, 0.5H).

EXAMPLE 4

Preparation of N-[3-(3,4,5-trimethoxybenzoyl)phenyl] 2-(3-pyridinyl)-4-thiazolidinecarboxamide dihydrochloride

Step 1. N-tert butylcarbonyl-3-iodoaniline

3-Iodoaniline (25 g, 114.13 mmol) and di-tert-butyldicarbonate (24.89 g) were mixed in methylene dichloride at room temperature with stirring. Dimethylaminopyridine (50 mg) was then added and the mixture stirred at room temperature overnight. The mixture was poured into 0.1N HCl and the organic phase was separate, dried over sodium sulfate and the solvent evaporated. The material was purified by flash chromatography over silica gel and the resulting residue recrystallized from ethyl acetate/hexane to yield 26.11 g (75%) of N-tert-butylcarbonyl-3-iodoaniline as a white solid.

Step 2. N-tert-butylcarbonyl-3-tributyltin-aniline

N-tert-butylcarbonyl-3-iodoaniline (28.2 g, 92.5 mmoL), prepared as described above, hexabutyldictin (46.7 mL, 92.5 mmol), and tetrakis(triphenylphosphine)-palladium (2.13 g) in toluene were mixed at 80° C. over a 48 hour period. The mixture was shaken with an ethyl acetate-water mixture, the organic layer separated and the solvent evaporated. Hexane was added to the residue and the mixture was filtered through Celite. The filtrate was evaporated to 40 mL and the residue purified by flash chromatography on silica gel to yield N-tert-butylcarbonyl-3-tributyltin-aniline (22.6 g, 51%).

Step 3. N-tert-butylcarbonyl-3-(3,4,5-trimethoxybenzoyl)aniline

N-tert-butylcarbonyl-3-tributyltin-aniline (18.6 g, 38.58 mmol) and 3,4,5-trimethoxybenzoyl chloride (8.81 g, 38.19 mmol) were added to benzyl tetrakis(triphenylphosphine)palladium chloride (155 mg) in tetrahydrofuran with stirring and heated to 65° C. for 16 hours. Ethyl acetate (250 mL) was added and the organic layer separated and dried over sodium sulfate. The material was purified by flash chromatography over silica gel to yield 7.12 g (49.68%) N-tert-butylcarbonyl-3-(3,4,5-trimethoxybenzoyl)aniline.

Step 4. 3-(3,4,5-trimethoxybenzoyl)aniline

N-tert-butylcarbonyl-3-(3,4,5-trimethoxybenzoyl)aniline (7.10 g, 18.92 mmol), prepared as described above, was dissolved in acetic acid (125 mL, 1.4N) at room temperature. A solution of hydrochloric acid/acetic acid (20 mL) was added and the mixture allowed to stand for 45 minutes. Diethylether (800 mL) was added and the resulting precipitate filtered and dried to yield 3-(3,4,5-trimethoxybenzoyl)aniline (5.24 g, 85.7%) as a tan solid.

Step 5. N-[3-(3,4,5-trimethoxybenzoyl)phenyl] 2-(3-pyridinyl)-4-thiazolidinecarboxamide dihydrochloride The desired material was prepared using the method of example 3 except using 3-(3,4,5-trimethoxybenzoyl)aniline instead of 3-aminobenzophenone. NMR (CDCl$_3$, 300 MHz): δ3.18–3.55(m,2H), 3.75–3.85(m,9H), 4.31(m, 1H), 5.91(s,0.33H), 6.05(s, 0.66H), 7.06(m,2H), 7.49–7.59(m,2H), 7.85–8.02(m,2H), 8.12(br s, 0.33H), 8.18(br s, 0.66H), 8.55–8.67(m, 1H), 8.78–8.83(m, 1H), 8.96(d, 0.66H), 9.07(d, 0.33H). Mass Spectrum (FAB): 480 (M+1)$^+$.

EXAMPLE 5

Preparation of N-[3-(4-methoxybenzoyl)phenyl] 2-(3-pyridinyl)-4-thiazolidinecarboxamide dihydrochloride The desired material was prepared using the method of example 4, except using 4-methoxybenzoylchloride instead of 3,4,5-trimethoxybenzoylchloride. NMR (DMSO-d$_6$, 300 MHz): δ3.15–3.32 (c,1H), 3.45–3.55 (c,1H), 3.88(s,1H), 4.25–4.36(c,1H), 5.92(s, 0.33H), 6.05(s,0.67H), 7.12(d,2H, J=8 Hz), 7.38–7.45(c,1H), 7.49–7.56(c,1H), 7.75(d,2H,J=8 Hz), 7.83–8.10(c, 3H), 8.55(bd,0.67H, J=7.5 Hz), 8.62(bd, 0.33H, J=7.0 Hz), 8.78–8.82(m,1H), 8.90(d,2H, J=3 Hz), 9.06(d,2H, J=3 Hz), 10.66(bs,0.33H), 10.78(bs, 0.67H). Mass Spectrum (DCI/NH$_3$): 420 (M+1)$^+$.

EXAMPLE 6

Preparation of N-[3-(3,4-methylenedioxybenzoyl)phenyl] 2-(3-pyridinyl)-4-thiazolidinecarboxamide dihydrochloride.

The desired material was prepared using the method of example 4, except using 3,4-methylenedioxybenzoylchloride instead of 3,4,5-trimethoxybenzoylchloride. NMR (CDCl$_3$, 300 MHz): δ3.18 (m,1H), 3.44(c,1H), 4.28(m,1H), 5.91(s, 0.33H), 6.50(s,0.67H), 6.19(s, 2H), 7.09(d, 1H, J=8 Hz), 7.28–7.33(c, 2H), 7.36–7.45(c,1H), 7.48–7.55(c,1H), 7.85–8.09(c, 3H), 8.55–8.68(c, 1H), 8.79–8.85(m, 1H), 8.98(d, 0.67H), 9.08(d, 0.33H), 10.69(bs, 0.33H), 10.71(bs, 0.67H). Mass Spectrum (DCI/NH$_3$): 433 (M+1)$^+$.

EXAMPLE 7

Preparation of N-[3-(3,5-dimethoxybenzoyl)phenyl] 2-(3-pyridinyl)-4-thiazolidinecarboxamide dihydrochloride The desired material was prepared using the method of example 4, except using 3,5-dimethoxybenzoylchloride instead of 3,4,5-trimethoxybenzoylchloride. NMR (CDCl$_3$, 300 MHz): δ3.16–3.31(c, 1H), 3.45–3.55(m,1H), 3.30(s,6H), 4.28–4.35(m, 1H), 5.92(s,0.33H), 6.05(s,0.67H), 6.79–6.85(c, 3H), 7.45–7.59(m, 2H), 7.88–8.01(m, 2H), 8.01–8.15(m, 1H), 8.56–9.36(c, 3H), 10.73(bs, 1H). Mass Spectrum (DCI/NH$_3$): 450 (M+1)$^+$.

EXAMPLE 8

Preparation of N-[3-(3,4-dimethoxybenzoyl)phenyl] 2-(3-pyridinyl)-4-thiazolidinecarboxamide dihydrochloride The desired material was prepared using the method of example 4, except using 3,4-dimethoxybenzoylchloride instead of 3,4,5-trimethoxybenzoylchloride. NMR (CDCl$_3$, 300 MHz): δ3.10–3.50 (m,2H), 3.82 (s,3H), 3.88 (s,3H), 4.28 (m, 1H), 5.89 (s, 0.67H), 6.02 (s, 0.33H), 7.12 (d, 1H), 7.31–7.59 (c, 4H), 7.82–8.12 (c, 3H), 8.43–8.61 (c, 1H), 8.78–9.12 (c, 2H), 10.12 (s, 0.33H), 10.61 (s, 0.67H). Mass Spectrum (DCI/NH$_3$): 450 (M+1)$^+$.

EXAMPLE 9

Preparation of N-(3-benzoylphenyl]) 2-(3-pyridinyl)-4-dithiolanecarboxamide

Step 1. Methyl 2,3-dimercaptopropenate

To a flame dried 1 liter 3-neck flask was added 30 g (1.25 mol, 5.8 eq) of sodium spheres (rinsed with hexanes). The flask was equipped with an addition funnel and a reflux condenser. Anhydrous methanol (400 mL) was added to the sodium metal via the addition funnel in a dropwise fashion (Exothermic!) at such a rate so as to maintain a gentle reflux throughout the addition. Once all the sodium was in solution (approximately 45 minutes), the reaction was cooled to 0° C. and saturated with gaseous H$_2$S for 1 hr. During the course of the addition excess H$_2$S was neutralized by bubbling the bleed line through a trap containing a 10% solution of aqueous sodium hydroxide. A solution of 50.0 g (0.22 mol, 1 eq.) 2,3-dibromopropionic acid dissolved in 100 ml of methanol was added to the reaction mixture via the addition funnel at a rapid drip rate. The solution was allowed to warm to room temperature and was stirred an additional 18 hr.

The reaction was then acidified to pH=2 by initial dropwise addition of 100 mL of saturated methanolic HCl (H$_2$S evolution observed) followed by bubbling gaseous HCl into the reaction mixture until the desired pH was obtained. At this point, a thick white precipitate was present. The solution was allowed to stir for an additional 4 hours and then concentrated on a rotoevaporator to remove the methanol. The resulting pasty residue was partitioned between 300 mL of water and 300 mL of ethyl ether. The aqueous phase was extracted with ethyl ether (2×) and the combined organic extracts washed once with brine and dried over magnesium sulfate. The drying agent was filtered off and the filtrate concentrated in vacuo. Yield: 28.5 g, 86.5%, light yellow oil.

Step 2. Methyl 2-(3-pyridinyl)-4-dithiolanecarboxylate

To a 3-neck round bottomed flask equipped with a Dean Stark trap and a constant rate addition funnel was added 7.05 g (65.7 mmol, 1.0 eq.) of 3-pyridinealdehyde and 15.0 g (78.9 mmol, 1.2 eq.) p-toluenesulfonic acid in 350 mL of toluene, 25 ml of 2-butanol, and 15 ml 1-butanol. The solution was heated to reflux, whereupon 10.0 g (65.7 mmol, 1 eq.) of the material prepared as in step 1, above, in 30 mL toluene was added dropwise over ninety minutes to the refluxing reaction mixture via the addition funnel. The reaction was allowed to reflux overnight and the following day cooled to room temperature and concentrated in vacuo. The residue was partitioned between saturated aqueous sodium bicarbonate and ethyl acetate (requires agitation for >30 min). The aqueous phase was extracted one more time with ethyl acetate. The combined organic extracts were then washed successively with saturated aqueous sodium bisulfite (×2), 1M aqueous sodium hydroxide (×2), and saturated aqueous brine (×1), dried over sodium sulfate, filtered and concentrated in vacuo to afford 18.57 g (117% crude yield) of a brown oil. TLC showed predominantly desired material along with some nicotinaldehyde and a much less polar impurity. The oil was purified by flash chromatography ($SiO_2$, 80:20 hexanes:ethyl acetate). The desired dithiolane was isolated in fractions 85–195 as 8.03 g (50.6% yield) of an orange oil. NMR $\delta(CDCl_3)$ 3.45 (dd, 0.5H), 3.6 (dd, 0.5H), 3.65 (dd, 0.5H), 3.7 (dd, 0.5H), 3.8 (s, 1.5H), 3.82 (s, 1.5H), 4.5 (t, 0.5H), 5.65 (s, 0.5H), 5.75 (s, 0.5H), 7.3 (dd, 1H), 7.95 (ddt, 1H), 8.5 (td, 1H), 8.7 (dd, 1H).

Step 3. 2-(3-pyridinyl)-4-dithiolanecarboxylic acid

Dithiolane ester (2 g, 8.3 mmol, 1 eq.), prepared as in step 2 above, was dissolved in a 3:1 (v/v) solution of THF and $H_2O$ and 432 mg of lithium hydroxide hydrate (10 mmol, 1.2 eq.) added in one portion. The reaction immediately assumes an orange color. After 10 min TLC shows complete consumption of starting ester. The reaction was concentrated in vacuo to remove THF and the resulting aqueous solution extracted with ether (2×) to remove any impurities. The aqueous phase was acidified to pH=4 with 1N aqueous HCl and concentrated in vacuo. The resulting oily residue was then ultrasonicated with THF and ethanol and vacuum filtered. The filtrate was concentrated in vacuo and chased two times with toluene to afford 1.6 g (85% yield) of a yellow solid.

Step 4. N-(3-benzoylphenyl) 2-(3-pyridinyl)-4-dithiolanecarboxamide

The desired material was prepared using the method of example 1, except using 2-(3-pyridinyl)-4-dithiolanecarboxylic acid, prepared as described in step 3 above, instead of 2-(3-pyridinyl)-4-thiazolidinecarboxylic acid. NMR ($CDCl_3$, 300 MHz): $\delta$4.0 (dd, 0.5H, J=3, 13 Hz), 4.17 (dd, 0.5H, J=2, 13 Hz), 4.55 (dd, 0.5H, J=2, 6 Hz), 4.73 (dd, 0.5H, J=3, 6 Hz), 5.79 (s, 1H), 7.3 (m, 1H), 7.45–7.65 (c, 5H), 7.8–7.95 (c, 5H), 8.55 (d, 1H, J=5 Hz), 8.7 (d, 1H, J=3 Hz), 8.97 (br d, 1H, J=7 Hz). IR ($CDCl_3$): 3700, 3320, 1680, 1660, 1600, 1590, 1530. Mass Spectrum ($DCI/NH_3$): 407 $(M+1)^+$, 423 $(M+NH_4)^+$.

EXAMPLE 10

Preparation of N-[3-(3,4,5-trimethoxybenzoyl)phenyl] 2-(3-pyridinyl)-4-dithiolanecarboxamide.

The desired material was prepared by the procedure of example 9, except using 3-(3,4,5-trimethoxybenzoyl)aniline, prepared as described in example 4, instead of 3-benzoylaniline. NMR ($CDCl_3$, 300 MHz): $\delta$3.55 (dd, 0.66H, J=5, 14 Hz), 3.63 (dd, 0.33H, J=5, 13 Hz), 3.85 (s, 6H), 3.95 (s, 3H), 4.0 (dd, 0.33H, J=3, 12 Hz), 4.15 (dd, 0.66H, J=3, 12 Hz), 4.55 (dd, 0.66H, J=3, 6 Hz), 4.75 (dd, 0.33H, J=3, 6 Hz), 5.77 (s, 0.66H), 5.78 (s, 0.33H), 7.1 (d, 2H, J=3 Hz). 7.3 (m, 1H), 7.45–7.6 (m, 2H), 7.75–8.0 (c, 3H), 8.55 (m, 1H), 8.73 (m, 1H). IR ($CDCl_3$): 3400, 2900, 1690, 1650, 1580, 1530, 1330, 1130. Mass Spectrum ($DCI/NH_3$): 497 (M+1).

EXAMPLE 11

Preparation of N-(3-benzoylphenyl) 2-(3-pyridinyl)-3-formyl-4-thiazolidinecarboxamide The desired material was prepared using the method of example 2, except using formic acetic anhydride instead of di-tert-butyl dicarbonate. NMR ($CDCl_3$, 300 MHz): $\delta$3.33 (dd, 1H, J=8.5, 11.0), 3.86 (dd, 1H, J=6.0, 12.5), 5.16 (dd, 1H, J=4.5, 7.0), 6.16 (s, 1H), 7.28 (dd, 1H, J=4.0, 8.5), 7.31–7.62 (c, 6H), 7.76–7.92 (c, 4H), 8.38 (s, 1H), 8.56 (dd, 1H, J=1.5, 4.5), 8.68 (s, 1H), 9.21 (s, 1H). IR ($CDCl_3$): 1695, 1655. Mass Spectrum ($DCI/NH_3$): 418 $(M+H)^+$.

EXAMPLE 12

Preparation of N-(3-benzoylphenyl) 2-(3-pyridinyl)-3-(N-methylcarbamoyl)-4-thiazolidinecarboxamide The desired material was prepared using the method of example 2, except using methylisocyanate instead of di-tert-butyl dicarbonate. NMR ($CDCl_3$, 300 MHz): $\delta$2.69–2.76 (c, 1½H), 2.82 (d, 1½H, J=4.5 Hz), 3.28 (dd, 1H, J=6 Hz, 12 Hz), 3.67 (d, ½H, J=4.5 Hz), 3.71 (d, ½H, J=4.5 Hz), 4.58 (d, ½H, J=4.5 Hz), 4.66 (d, ½H, J=4.5 Hz), 5.21 (dd, 1H, J=1.5 Hz, 4.5 Hz), 5.95 (s, ½H), 6.11 (s, ½H), 7.28–7.65 (c, 7H), 7.76–7.85 (c, 2H), 7.89–7.95 (c, 2H), 8.50–8.61 (c, 1H), 8.68 (d, 1H, J=1.5 Hz), 9.51 (s, ½H), 9.60 (s, ½H). IR ($CDCl_3$): 1535(br), 1660(s), 1690(s), 3300(br), 3460(w). Mass Spectrum ($DCI/NH_3$): 447(M+H)+, 390, 250, 198.

EXAMPLE 13

Preparation of N-(3-benzoylphenyl) 2-(3-pyridinyl)-thiazolid-4-ylacetamide

Step 1.
2-(3-pyridinyl)-3-(tert-butoxycarbonyl)-thiazolid-4-yl diazomethylketone N-methyl morpholine (0.89 mL) was added to a solution of 2-(3-pyridinyl)-3-(tert-butoxycarbonyl)-4-thiazolidinecarboxylic acid prepared as in example 2, step 1 (2.52 g, 8.1 mmol) in dry THF (50 mL) at 0° C. Isobutyl chloroformate (1.1 mL) was then added. The mixture was stirred for 15 min then filtered and the solid washed with THF (2×25 mL). The pink filtrate was added to a solution of diazomethane (~0.3M, 250 mL) at −0° C. The orange solution was allowed to be stirred for an addition 10 minutes and then the cooling bath was removed so that the mixture warmed to room temperature over 2 hours. The mixture was purged with nitrogen and then the solvent was removed in vacuo. The residue was chromatographed on silica gel, eluting with ethyl acetate:hexanes (1:1) to afford the desired material as a thick orange oil (52%, 1.4 g).

Step 2. Methyl [2-(3-pyridinyl)-3-tert-butoxycarbonyl]thiazolid-4-ylacetate

A solution of silver benzoate (1.0 g in 10 mL of triethyl amine) was added to a solution of 2-(3-pyridinyl)-3-(tert-butoxycarbonyl)-thiazolid-4-yl diazomethylketone (1.4 g, 4.2 mmol) in methanol (50 mL). The mixture was stirred for 2 hours and the solvent was removed in vacuo. The residue was partitioned between ethyl acetate and water. The organic phase was dried over magnesium sulfate and concentrated. The residue was purified by chromatography on silica gel eluting with hexane:ethyl acetate (3:1) to give 0.78 g (55%) of the desired product.

Step 3.
[2-(3-pyridinyl)-3-tert-butoxycarbonyl]thiazolid-4-ylacetic acid

Lithium hydroxide monohydrate (90 mg, 1.1 eq) was added to a solution of methyl [2-(3-pyridinyl)-3-tert-butoxycarbonyl]thiazolid-4-ylacetate (0.66 g, 1.95 mmol) in methanol (8 mL) and water (2 mL) and the mixture was allowed to stir at room temperature for 4 hours. The solvent was removed and the residue partioned between water and ethyl acetate. The aqueous phase was washed with ethyl acetate and acidified to pH ~ 4 with 2M HCl. Chloroform:isopropanol (9:1) was added. The organic phase was concentrated to give 0.6 g of the desired material.

Step 4. N-(3-benzoylphenyl) 2-(3-pyridinyl)-3-tert-butoxycarbonyl-thiazolid-4-ylacetamide N-methylmorpholine (0.4 mL) and isobutyl chloroformate (0.25 mL) were added to a solution of [2-(3-pyridinyl)-3-tert-butoxycarbonyl]thiazolid-4-ylacetic acid (0.57 g, 1.76 mmol) in DMF (6 mL) and methylene chloride (15 mL) at 0° C. The mixture was stirred for 10 minutes and then 3-aminobenzophenone hydrochloride (0.45 g) and N-methylmorpholine (0.2 mL) in methylene chloride (5 mL) was added. The mixture was allowed to be stirred for 23 hours and the solvent was removed in vacuo. The residue was partitioned between water and ethyl acetate. The organic phase was washed with saturated aqueous sodium bicarbonate solution and brine then dried over magnesium sulfate. The solvent was removed and the residue chromatographed on silica gel, eluting with ethyl acetate hexanes (6:4) to afford the desired material (66%).

Step 5: N-(3-benzoylphenyl) 2-(3-pyridinyl)-thiazolid-4-ylacetamide

Hydrochloric acid in dioxane (4M, 10 mL) was added to N-(3-benzoylphenyl) 2-(3-pyridinyl)-3-tert-butoxycarbonyl-thiazolid-4-ylacetamide and the mixture stirred at 0° C. for 2 hours. The solvent was removed and the residue partitioned between water and ether. The aqueous phase was made basic with sodium carbonate and extracted with methylene chloride. This organic phase was dried with magnesium sulfate and the solvent was evaporated. The material was purified by flash chromatography on silica gel eluting with chloroform:methanol (95:5) to give 0.177 g (87%) of the desired compound. NMR (CDCl$_3$, 300 MHz): δ2.68 (dd, 1H, J=5.0, 15.0), 2.76 (dd, 1H, J=7.0, 15.0), 2.84–2.93 (c, 2H), 3.36 (m, 1H), 3.71 (m, 0.5H), 4.01 (m, 0.5H), 5.62 (s, 0.5H), 5.73 (5, 0.5H), 7.30 (m, 1H), 7.49–7.61 (c, 5H), 7.77–7.92 (c, 5H), 8.56 (dd, 0.5H, J=1.0, 5.0), 8.59 (dd, 0.5H, J=1.0, 5.0), 8.78 (m, 1H), 9.05 (bs, 0.5H), 9.35 (bs, 0.5H). IR (CDCl$_3$): 1685, 1660. Mass Spectrum (DCI/NH$_3$): 404 (M+H)$^+$.

EXAMPLE 14

Preparation of N-(3-benzoylphenyl) 2-(3-pyridinyl)-3-carbamoylthiazolid-4-ylacetamide To a solution of N-(3-benzoylphenyl) 2-(3-pyridinyl)-thiazolid-4-ylacetamide (108 mg, 0.26 mmol) prepared as described in example 13, in dioxane (2.6 mL) was added trimethylsilylisocyanate (128 μL, 85%) at room temperature and under nitrogen. This solution was then heated to 60° for 6 hours, then cooled to room temperature and an addition portion of trimethylsilyl isocyanate was added. This solution was again heated at 60° C. for 6 hours then cooled to room temperature and partitioned between ethyl acetate (10 mL) and brine (5 mL). The aqueous phase was extracted with ethyl acetate then the organic layers were combined, washed with brine and dried over magnesium sulfate. This was filtered and concentrated to give an orange oil which was purified by flash chromatography on silica gel eluting with chloroform:methanol 95:5. The desired material was obtained as a white foam. NMR δ (CDCl$_3$): 2.80 (dd, 1H, J=4.5, 13.0), 2.93 (dd, J=1.0, 13.0), 3.07 (dd, 1H, J=8.0, 12.0), 3.41 (dd, 1H, J=6.0, 11.0), 5.08 (m, 1H), 5.35 (bs, 2H), 6.41 (s, 1H), 7.20 (dd, 1H, J=6.0, 9.0), 7.38–7.52 (c, 4H), 7.58 (tt, 1H, J=0.5, 6.0), 7.71 (d, 1H, J=8.0), 7.78–7.88 (c, 3H), 8.37 (bs, 1H), 8.48 (d, 1H, J=3.0), 8.70 (d, 1H, J=2.0) IR (CHCl$_3$) 1660, 1595. Mass Spec (DCI-NH$_3$): 447 (M+H)$^+$ 404 Exact Mass: 447.148 (Experimental); 447.149 (Theoretical).

EXAMPLE 15

Preparation of N-(3-benzoylphenyl) N-methyl 2-(3-pyridinyl)-4-thiazolidinecarboxamide dihydrochloride Step 1. N-(3-benzoylphenyl) N-methyl 2-(3-pyridinyl)-3-tert-butoxycarbonyl-4-thiazolidinecarboxamide Lithium hexamethyl disilazide (0.6 mL, 1.0M in hexanes) was added at 0° C. under nitrogen to a solution of N-(3-benzoylphenyl) 2-(3-pyridinyl)-3-tert-butoxycarbonyl-4-thiazolidinecarboxamide prepared as described in example 2 (202 mg, 0.41 mmol), in dry THF (4 mL, 0.1 mL). The mixture was stirred for 20 min then methyl iodide (25 μL) was added and the mixture stirred for an additional 8 hours. The reaction mixture was partioned between ethyl acetate and saturated sodium bicarbonate solution. The organic phase was dried over magnesium sulfated and the solvent removed in vacuo. The residue was purified by flash chromatography eluting with hexanes:ethyl acetate (12:3) to yield the desired product (0.53 g, 45%).

Step 2. N-(3-benzoylphenyl) N-methyl 2-(3-pyridinyl)-4-thiazolidinecarboxamide dihydrochloride Hydrochloric acid in dioxane (4M, 10 mL) was added to N-(3-benzoylphenyl) N-methyl 2-(3-pyridinyl)-3-tert-butoxycarbonyl-4-thiazolidinecarboxamide (0.64 g) in dioxane (3 mL). The reaction mixture was concentrated and the residue partitioned between ethyl acetate and saturated aqueous sodium carbonate. The organic layer was washed with saturated aqueous sodium carbonate and dried over magnesium sulfate. The solvent was removed in vacuo and the residue chromatographed on silica gel, eluting with ethyl acetate to give the desired compound as a colorless oil (417 mg, 81%). This was converted to the dihydrochloride salt using the method of example 3. NMR (CDCl$_3$, 300 MHz): δ2.72–3.28 (c, 3H), 3.42–3.97 (c, 4H), 5.57 (s, 0.6H), 5.61 (s, 0.4H), 7.21–7.48 (c, 6H), 7.81 (m, 1H), 8.51 (dd, 0.4H, J=1.0, 8.0), 8.56 (dd, 0.6H, J=1.0, 8.0), 8.72 (m, 1H). Mass Spectrum (DCI/NH$_3$): 286 (M+H)$^+$.

EXAMPLE 16

N-[3-(3,4,5-trimethoxybenzoyl)phenyl] N-methyl 2-(3-pyridinyl)-4-dithiolanecarboxamide hydrochloride The desired material was prepared according to the method of example 15, except using N-[3-(3,4,5-trimethoxybenzoyl)phenyl]2-(3-pyridinyl)-4-dithiolanecarboxamide, prepared as described in example 9 instead of N-(3-benzoylphenyl) 2-(3-pyridinyl)-3-tert-butoxycarbonyl-4-thiazolidinecarboxamide. NMR (CDCl$_3$, 300 MHz): δ3.35 (s, 3H), 3.45 (m, 2H), 3.85 (d, 6H), 3.95 (d, 3H), 4.35 (m, 0.5H), 4.5 (t, 0.5H), 5.29 (s, 1H), 7.05 (d, 2H, J=6 Hz), 7.23 (m, 1H), 7.3 (m, 1H), 7.51 (m, 1H), 7.60 (m, 1H), 7.73 (bs, 1H), 7.80 (m, 1H), 8.52 (d, 1H, J=6 Hz), 8.64 (d, 1H, J=12 Hz). Mass Spectrum (DCI/NH$_3$): 511 (M+H)$^+$.

EXAMPLE 17

Preparation of N-(3-benzoylphenyl) N'-[2-(3-pyridinyl)dithiolan-4-yl] urea

Diphenylphosphoryl azide (0.46 mL. 2.1 mmol) was added to a solution N-methyl morpholine (2.1 mmol) and 2-(3-pyridinyl)-4-dithiolanecarboxylic acid, prepared as described in example 9 (0.44 g, 1.95 mmole) in THF (20 mL). The mixture was heated at 70° C. for 1 hour and then 3-aminobenzophenone (0.58 g, 2.93 mmole) was added. The mixture was heated at 70° C. for an additional 90 min and then cooled to room temperature. The mixture was concentrated and the residue disolved in ethyl acetate. This solution was washed with sodium bicarbonate, dried over sodium sulfate and the solvent was removed in vacuo. The residue was chromatographed by flash chromatography eluting with ethyl acetate:hexanes (7:3) to yield the two separable products corresponding to cis and trans ring substitution of the desired material (assignment not known). NMR (CDCl$_3$, 300 MHz): δ3.36 (dd, 1H, J=1.0, 11.5), 3.48 (dd, 1H, J=4.5, 11.5), 5.61 (s, 1H), 6.13 (ddd, 1H, J=1.0, 4.5, 9.0), 6.30 (b d, 1H, j=9.0), 7.21 (dd, 1H, J=5.0, 9.0), 7.37-7.67 (c, 6H), 7.76-7.84 (c, 5H), 8.50 (dd, 1H, J=1.0, 6.0), 8.78 (d, 1H, J=1.0). Mass Spectrum (DCI/NH$_3$): 422 (M+H)$^+$, 241, 199. NMR (CDCl$_3$, 300 MHz): δ3.28 (d, 1H, J=12.0), 3.52 (b d, 1H, J=12.0), 5.55 (s, 1H), 6.29 (b s, 2H), 7.26 (m, 1H), 7.36-7.51(c, 4H), 7.58 (m, 1H), 7.69 (d, 1H, J=11.0), 7.72-7.88 (c, 5H), 8.50 (dd, 1H, 1.5, 6.0), 8.59 (d, 1H, J=1.5). Mass Spectrum (DCI/NH$_3$): 422 (M+H)$^+$, 241, 199.

EXAMPLE 18

Preparation of N-[3-(3,4,5-trimethoxybenzoyl)phenyl] N'-[2-(3-pyridinyl)dithiolan-4-yl] urea The desired material was prepared according to the method of example 17, except using 3-(3,4,5-trimethoxybenzoyl)aniline, prepared as described in example 4 instead of 3-benzoylaniline. NMR (CDCl$_3$, 300 MHz): δ3.37(bd, 1H, J=12.5), 3.50(dd, 1H, J=4.0, 12.5), 3.86(s, 6H), 3.94(s, 3H), 5.62(s, 1H), 6.11-6.19 (c, 2H), 7.09 (s, 2H), 7.22(dd, 1H, J=5.0, 9.0), 7.38-7.46(c, 3H), 7.55(bs, 1H), 7.69-7.73(c, 2H), 7.81(dt, 1H, J=1.5, 9.0), 8.51(dd, 1H, J=1.5, 4.5), 8.79(d, 1H, J=1.5). Mass Spectrum (FAB): 512 (M+1)$^+$. NMR (CDCl$_3$, 300 MHz): δ3.30(dd, 1H, J=2.0, 12.0), 3.52(dd, 1H, J=4.5, 12.0), 3.88(s, 6H), 3.96(s, 3H), 5.59(s, 1H), 6.06(d, 1H, J+9.0), 6.28(dq, 1H, J=2.0, 9.0), 7.10(s, 2H), 7.28(dd, 1H, J=6.0, 8.0), 7.38(bs,1H), 7.40-7.48(c, 3H), 7.69-7.77(c 2H), 7.81(dt, 1H, J=1.5,8.0), 8.51(dd, 1H, J=1.0, 6.0), 8.62(d, 1H, J=2.0). Mass Spectrum (DCI/NH$_3$): 512(M+1)$^+$, 314.

EXAMPLE 19

Preparation of N-methyl-N-(3-benzoylphenyl) N'-[2-(3-pyridinyl)dithiolan-4-yl] urea

Step 1. N-tert-butoxycarbonyl-N-methyl-3-aminobenzophenone

N-tert-butoxycarbonyl-3-aminobenzophenone (2 g, 6.7 mmol) in DMF (15 mL) was added to a suspension of sodium hydride (0.54 g, 13.5 mmol) in DMF (70 mL) and the mixture was stirred at 0° C. for 40 minutes. Dimethylsulfate (1.3 mL, 13.5 mmol) was added and the mixture stirred at room temperature for 15 hours. The mixture was partitioned between ethyl acetate and saturated NaCl. The organic layer was dried over sodium sulfate, filtered and concentrated in vacuo to afford the desired material as an orange oil.

Step 2. N-methyl-3-amino benzophenone

Hydrochloric acid in dioxanes (4M, 7 mL) was added to a solution of N-tert-butoxycarbonyl-N-methyl-3-aminobenzophenone (2.2 g, 7.4 mmol) in methylene chloride (5 mL). The mixture was stirred at room temperature for 1 hour and then concentrated. The residue was partitioned between chloroform and saturated sodium bicarbonate solution and the organic layer was washed with saturated sodium chloride and dried over sodium sulfate. The solvent was removed in vacuo to yield the desired product.

Step 3. N-methyl-N-(3-benzoylphenyl) N'-[2-(3-pyridinyl)dithiolan-4-yl] urea The desired material was prepared using the method of example 17, except using N-methyl-3-aminobenzophenone instead of 3-aminobenzophenone. NMR (CDCl$_3$, 300 MHz): δ3.2 (dd, 1H, J=3, 13 Hz), 3.35 (s, 3H), 3.45 (dd, 1H, J=4, 13 Hz), 5.32 (br d, 1H, J=9 Hz), 5.55 (s, 1H0, 6.23 (ddd, 1H, J=2, 4, 9 Hz), 7.25 (dd, 1H, J=5, 8 Hz), 7.5-7.85 (c, 10H), 8.5 (dd, 1H, J=2, 5 Hz), 8.63 (d, 1H, J=3 Hz). IR (CDCl$_3$): 1660, 1490. Mass Spectrum (DCI/NH$_3$): 436(M+1)+, 330, 298. NMR (CDCl$_3$, 300 MHz): δ3.32 (dd, 1H, J=1, 8 Hz), 3.37 (s, 3H), 3.45 (dd, 1H, J=2, 8 Hz), 5.33 (dd, 1H, J=6 Hz), 5.6 (s, 1H), 6.1 (ddd, 1H, J=1, 2, 6 Hz), 7.2 (dd, 1H, J=2, 5 Hz), 7.5 (dd, 2H, J=5, 5 Hz), 7.55 (m, 1H), 7.63 (br dd, 3H, J=5, 5 Hz), 7.8 (dd, 4H, J=5 Hz), 8.5 (td, 1H, J=1, 3 Hz), 8.57 (d, 1H, J=1 Hz). IR (CDCl$_3$): 300 (weak), 1660, 1420. Mass Spectrum (DCI/NH$_3$): 436(M+1)$^+$, 238.

EXAMPLE 20

Preparation of N-methyl-N-[3-(3,4,5-trimethoxybenzoyl)phenyl] N'-[2-(3-pyridinyl)dithiolan-4-yl] urea The desired material was prepared according to the method of example 19, except using N-tert-butoxycarbonyl-3-(3,4,5-trimethoxy)benzoylaniline instead of 3-aminobenzophenone. NMR (CDCl$_3$, 300 MHz): δ3.29 (dd, 1H, J=3 Hz, J=15 Hz), 3.37 (s, 3H), 3.45 (dd, 1H, J=6 Hz, J=21 Hz), 3.85 (s, 6H), 3.95 (s, 3H), 5.33 (d, 1H, J=15 Hz), 5.6 (s, 1H), 6.08 (ddd, 1H, J=3 Hz), J=6 Hz, J=12 Hz), 7.05 (s, 2H), 7.23 (m, 1H), 7.52 (dd, 1H, J=9 Hz), 7.62 (m, 2H), 7.75 (d, 2H), 8.49 (d, 1H, J=6 Hz), 8.57 (s, 1H). IR (CDCl$_3$): 1660(C=0, ketone), 1580, 1500. Mass Spectrum (DCI/NH₃): 526(M+H)⁺.
NMR (CDCl₃, 300 MHz): δ3.23 (dd, 1H, J=3 Hz,
J=12 Hz), 3.35 (s, 3H), 3.45 (dd, 1H, J=6 Hz), 3.88 (s,
6H), 3.97 (s, 3H), 5.33 (d, 1H, J=12 Hz), 5.59 (s, 1H),
6.62 (ddd, 1H, J=3 Hz, J=7 Hz, J=10 Hz), 7.1 (s, 2H),
7.30 (m, 1H), 7.51 (d, 1H, J=10 Hz), 7.59 (t, 1H, J=6
Hz, J=15 Hz), 7.72 (d, 1H, J=10 Hz), 7.85 (d, 1H, J=7
Hz), 8.5 (d, 1H, J=6 Hz), 8.67 (s, 1H). IR (CDCl₃):
1660(C=O, ketone), 1580, 1500. Mass Spectrum
(DCI/NH₃): 526 (M+H)⁺.

EXAMPLE 21

Preparation of
N-(3-benzoylphenyl)-2-(3-pyridyl)-5-pyrrolidinecarboxamide

Step 1.
2,3-dehydro-2-(3-pyridyl)-5-pyrollidinecarboxylic acid

The title material was prepared as described by Abbaspour, Hecht, Hoffman, J. Org. Chem. 1987, 52, 3474-3477.

Step 2.
N-(3-benzoylphenyl)-2,3-dehydro-2-(3-pyridyl)-5-pyrrolidinecarboxamide

The title material was prepared according to the method of example 1, except using the material prepared in step 1 above instead of 2-(3-pyridinyl)-4-thiazolidinecarboxylic acid.

Step 3.
N-(3-benzoylphenyl)-2-(3-pyridyl)-5-pyrrolidinecarboxamide

The material prepared as in step 2, above was reduced with hydrogen and 10% palladium on carbon to give the desired product. NMR (CDCl₃, 300 MHz): δ2.45 (m, 1H), 2.65 (m, 3H), 4.8 (dd, 1H, J=4.5 Hz, J=10.5 Hz), 5.15 (dd, 1H, J=7.5 Hz, J=12.0 Hz), 7.55 (m, 4H), 7.65 (m, 1H), 7.90 (m, 1H), 8.2 (m, 2H), 8.95 (m, 2H), 9.2 (s, 1H). Mass Spectrum (DCI/NH₃): 372(M+H)⁺, 147.

What is claimed is:
1. A compound of the formula:

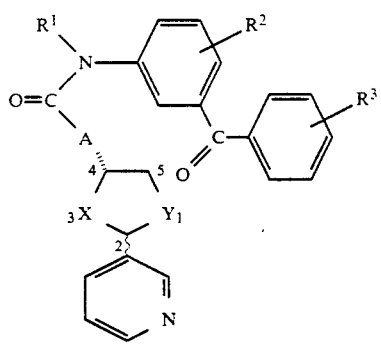

a separate stereoisomeric form or mixtures thereof, or a pharmaceutically acceptable salt thereof wherein
A is a valence bond or is selected from the group consisting of a) methylene, and (b) >NR⁴ wherein R⁴ is hydrogen or alkyl of from one to six carbon atoms;
X is >NR⁵ where R⁵ is selected from the group consisting of
hydrogen,
alkyl of from one to six carbon atoms,
alkoyl of from one to six carbon atoms,
—C(O)NR⁶R⁷ where R⁶ and R⁷ are independently selected from hydrogen and alkyl of from one to six carbon atoms, and
—C(O)OR⁸ where R⁸ is an alkyl radical of from one to six carbon atoms;
Y is sulfur;
R¹ is selected from the group consisting of
(a) hydrogen, and
(b) alkyl of from one to six carbon atoms,
R² is one, two, or three substituents selected from the group consisting of
(a) hydrogen,
(b) halogen, and
(c) alkyl of from one to six carbon atoms;
R³ is one, two, or three substituents selected from the group consisting of
(a) hydrogen,
(b) halogen, and
(c) alkoxy of from one to six carbon atoms;
2. A compound as claimed in claim 1 having the formula:

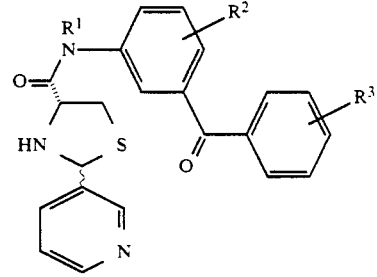

wherein R¹, R², and R³ are defined therein.
3. A compound as defined by claim 2 in which R¹ and R² are independently selected from hydrogen and alkyl of from one to six carbon atoms and R³ is hydrogen or alkoxy from one to six carbon atoms or a pharmaceutically acceptable salt thereof.
4. A compound as defined by claim 2 in which R¹ is hydrogen or methyl; R² is hydrogen and R³ is hydrogen, dimethoxy or trimethoxy or a pharmaceutically acceptable salt thereof.
5. A compound as defined by claim 2 selected from the group consisting of
N-(3-benzoylphenyl)2-(3-pyridinyl)-4-thiazolidine carboxamide;
N-(3-benzoylphenyl)2-(3-pyridinyl)-3-tert-butoxycarbonyl-4 thiazolidinecarboxamide;
N-[3-(4-methoxybenzoyl)phenyl]2-(3-pyridinyl)-4-thiazolidinecarboxamide;
N-[3-(3,4-dimethoxybenzoyl)phenyl]-2-(3-pyridinyl)-4-thiazolidinecarboxamide
N-[3-(3,5-dimethoxybenzoyl)phenyl]2-(3-pyridinyl)-4-thiazolidinecarboxamide;
N-[3-(3,4,5-trimethoxybenzoyl)phenyl]2-(3-pyridinyl)-4-thiazolidinecarboxamide;
N-(3-benzoylphenyl)N-methyl2-(3-pyridinyl)-4-thiazolidinecarboxamide;
N-(3-benzoylphenyl)2-(3-pyridinyl)-3-formyl-4-thiazolidinecarboxamide;
N-(3-benzoylphenyl)2-(3-pyridinyl)-3-(N-methylcarbamoyl)-4-thiazolidinecarboxamide; or
a pharmaceutically acceptable salt thereof.
6. A pharmaceutical composition useful for inhibiting PAF in a mammal in need of such treatment comprising a PAF-inhibitive effective amount of a compound as defined by claim 1 in combination with a pharmaceutically acceptable carrier.

* * * * *